US00PP28559P2

(12) United States Plant Patent
Konst

(10) Patent No.: US PP28,559 P2
(45) Date of Patent: Oct. 24, 2017

(54) ***ALSTROEMERIA* PLANT NAMED 'KONCAREPLY'**

(50) Latin Name: *Alstroemeria hybrida*
Varietal Denomination: Koncareply

(71) Applicant: Johannes Wilhelmus Maria Konst, Nieuwveen (NL)

(72) Inventor: Johannes Wilhelmus Maria Konst, Nieuwveen (NL)

(73) Assignee: KONST BREEDING B.V., Nieuwveen (NL)

( * ) Notice: Subject to any disclaimer, the term of this patent is extended or adjusted under 35 U.S.C. 154(b) by 0 days.

(21) Appl. No.: 15/330,209

(22) Filed: Aug. 22, 2016

(51) Int. Cl.
*A01H 5/02* (2006.01)

(52) U.S. Cl.
USPC ..... Plt./309

(58) Field of Classification Search
USPC ..... Plt./309
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Alstroemeria* plant named 'Koncareply', characterized by its compact and mounding plant habit; sturdy and strong plants; vigorous growth habit and rapid growth rate; freely branching habit; numerous purple violet-colored flowers with darker-colored stripes; and good garden performance.

2 Drawing Sheets

Botanical designation: *Alstroemeria hybrida.*
Cultivar denomination: 'KONCAREPLY'.

BACKGROUND OF THE INVENTION

The present invention relates to a new and distinct cultivar of *Alstroemeria* plant, botanically known as *Alstroemeria hybrida*, typically grown as a container-type garden *Alstroemeria* and hereinafter referred to by the name 'Koncareply'.

The new *Alstroemeria* plant is a product of a planned breeding program conducted by the Inventor in Nieuwveen, The Netherlands. The objective of the breeding program is to create new compact container-type garden *Alstroemeria* plants that have an early and freely flowering habit with attractive leaf and flower coloration.

The new *Alstroemeria* plant originated from a cross-pollination made by the Inventor in Nieuwveen, The Netherlands in April, 2011 of a proprietary selection of *Alstroemeria hybrida* identified as code number 43573-3, not patented, as the female, or seed, parent with a proprietary selection of *Alstroemeria hybrida* identified as code number 43629-2, not patented, as the male, or pollen, parent. The new *Alstroemeria* plant was discovered and selected by the Inventor as a single flowering plant from within the progeny of the stated cross-pollination in a controlled greenhouse environment in Nieuwveen, The Netherlands in September, 2012.

Asexual reproduction of the new *Alstroemeria* plant by in vitro rhizogenesis in a controlled greenhouse environment in Nieuwveen, The Netherlands since June, 2014 has shown that the unique features of this new *Alstroemeria* plant are stable and reproduced true to type in successive generations.

SUMMARY OF THE INVENTION

Plants of the new *Alstroemeria* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Koncareply'. These characteristics in combination distinguish 'Koncareply' as a new and distinct *Alstroemeria* plant:

1. Compact and mounding plant habit.
2. Sturdy and strong plants.
3. Vigorous growth habit and rapid growth rate.
4. Freely branching habit.
5. Numerous purple violet-colored flowers with darker-colored stripes.
6. Good garden performance.

Plants of the new *Alstroemeria* can be compared to plants of the female parent selection. Plants of the new *Alstroemeria* differ primarily from plants of the female parent selection in the following characteristics:

1. Plants of the new *Alstroemeria* have larger flowers than plants of the female parent selection.
2. Plants of the new *Alstroemeria* and the female parent selection differ in flower stripes as flowers of plants of the female parent selection have fewer stripes.

Plants of the new *Alstroemeria* can be compared to plants of the male parent selection. Plants of the new *Alstroemeria* differ primarily from plants of the male parent selection in flower color as plants of the male parent selection have pink-colored flowers.

Plants of the new *Alstroemeria* can be compared to plants of the *Alstroemeria hybrida* 'Koncayuko', disclosed in U.S. Plant Pat. No. 22,282. In side-by-side comparisons conducted in Nieuwveen, The Netherlands, plants of the new *Alstroemeria* differ from plants of 'Koncayuko' in the following characteristics:

1. Plants of the new *Alstroemeria* have larger and darker green-colored leaves than plants of 'Koncayuko'.

2. Plants of the new *Alstroemeria* flower earlier than plants of 'Koncayuko'.
3. Plants of the new *Alstroemeria* have larger inflorescences than plants of 'Koncayuko'.
4. Plants of the new *Alstroemeria* and 'Koncayuko' differ in flower color as plants of 'Koncayuko' have red purple-colored flowers.

BRIEF DESCRIPTION OF THE PHOTOGRAPHS

The accompanying colored photographs illustrate the overall appearance of the new *Alstroemeria* plant showing the colors as true as it is reasonably possible to obtain in colored reproductions of this type. Colors in the photographs may differ slightly from the color values cited in the detailed botanical description which accurately describe the colors of the new *Alstroemeria* plant.

The photograph on the first sheet is a side perspective view of a typical flowering plant of 'Koncareply' grown in container.

The photograph on the second sheet is a close-up view of a typical flower of 'Koncareply'.

DETAILED BOTANICAL DESCRIPTION

The aforementioned photographs and following observations and measurements describe plants of the new *Alstroemeria* grown during the late spring in 19-cm containers in a glass-covered greenhouse in Nieuwveen, The Netherlands and under cultural practices typical of commercial container-type *Alstroemeria* production. During the production of the plants, day temperatures ranged from 6° C. to 30° C. and night temperatures ranged from 6° C. to 20° C. Plants were 36 weeks old when the photographs and description were taken. In the following description, color references are made to The Royal Horticultural Society Colour Chart, 2015 Edition, except where general terms of ordinary dictionary significance are used.

Botanical classification: *Alstroemeria hybrida* 'Koncareply'.

Parentage:

*Female, or seed, parent*.—Proprietary selection of *Alstroemeria hybrida* identified as code number 43573-3, not patented.

*Male or pollen parent*.—Proprietary selection of *Alstroemeria hybrida* identified as code number 43629-2, not patented.

Propagation:

*Type*.—In vitro rhizogenesis.

*Root description*.—Thick, fleshy; typically white in color, actual color of the roots is dependent on substrate composition, water quality, fertilizers, substrate temperature and physiological age of roots.

*Rooting habit*.—Freely branching; dense.

*Rhizome description*.—Shape: Elongate; rounded. Length: About 5 cm. Diameter: About 8 mm. Texture: Smooth. Color: Close to 161D.

Plant description:

*Plant and growth habit*.—Perennial garden plant; compact and mounded; freely branching habit, bushy appearance; sturdy and strong plants; vigorous growth habit; rapid growth rate.

*Plant height*.—About 35 cm.

*Plant diameter* (*area of spread*).—About 40 cm.

Stem description:

*Aspect*.—Mostly upright.

*Internode length*.—About 1.4 cm to 2.3 cm.

*Strength*.—Strong, sturdy.

*Texture*.—Smooth, glabrous.

*Color*.—Close to 145B; distally, tinged with close to 177A.

Leaf description:

*Arrangement*.—Alternate; below the peduncle, arranged in a single whorl; leaves sessile.

*Length*.—About 6.5 cm to 11.5 cm.

*Width*.—About 1.4 cm to 3.2 cm.

*Shape*.—Lanceolate.

*Apex*.—Acute.

*Base*.—Attenuate.

*Margin*.—Entire.

*Texture and luster, upper and lower surfaces*.—Smooth, glabrous; slightly glossy.

*Venation pattern*.—Parallel.

*Color*.—Developing leaves, upper surface: Close to 141B. Developing leaves, lower surface: Close to 137B. Fully expanded leaves, upper surface: Close to 139A; venation, close to 144A. Fully expanded leaves, lower surface: Close to 137A; venation, close to 141B.

Flower description:

*Flower type and habit*.—Single cup-shaped flowers arranged in compound umbels; flowers face upright to outwardly; freely flowering habit with up to twelve flowers developing per inflorescence and about 40 to 75 flowers developing per plant during the flowering season.

*Natural flowering season*.—Flowering continuous from the late spring until the autumn in The Netherlands; early-flowering habit, plants begin flowering about 6 to 16 weeks after stem initiation.

*Fragrance*.—None detected.

*Flower longevity on the plant*.—About one to three weeks, longevity is temperature-dependent; flowers not persistent.

*Flower longevity as a cut flower*.—About one to two weeks, longevity is temperature-dependent; flowers not persistent.

*Flower buds*.—Length: About 5 cm. Diameter: About 1.5 cm. Shape: Ovoid. Color: Close to 72A; towards the apex, close to 187B; apex, close to 146A; venation, close to 143A.

*Umbel height*.—About 15 cm.

*Umbel diameter*.—About 18 cm.

*Flower diameter*.—About 5 cm.

*Flower depth* (*height*).—About 6 cm.

*Perianth*.—Arrangement: Six arranged in two whorls, each whorl with two lateral and one median segments. Size, inner perianth: Length, lateral segments: About 5.9 cm. Width, lateral segments: About 1.4 cm. Length, median segment: About 3.9 cm. Width, median segment: About 1.3 cm. Size, outer perianth: Length, lateral segments: About 4.2 cm. Width, lateral segments: About 2.5 cm. Length, median segment: About 4.5 cm. Width, median segment: About 2.4 cm. Shape, inner perianth, lateral and median segments: Lanceolate. Shape, outer perianth, lateral and median segments: Obovate. Apex, inner perianth, lateral and median segments: Acute. Apex, outer perianth, lateral and median segments: Emarginate, wishbone-shaped. Base, inner and outer perianths, lateral and median segments: Attenuate. Margin, inner and outer perianths, lateral and median segments: Proximally, entire; distally, finely serrate. Texture, inner and outer perianths, lateral and median segments: Smooth, glabrous. Luster, inner and outer perianths, lateral and median segments: Matte, dull. Color, inner perianth, lateral segments: When opening, upper surface: Towards the apex, close to N78A; mid-section, close to 4D; towards the base, close to 70B; stripes, close to 187A. When opening, lower surface: Towards the apex, close to N78A; towards the base, close to N78B; stripes, close to N200A. Fully opened, upper surface: Towards the apex, close to N80A; mid-section, close to 56D; towards the base, close to N78A and NN155D; stripes, close to N200A; color does not change with development. Fully opened, lower surface: Towards the apex, close to N80A; mid-section, close to 158C; towards the base, close to N81D; stripes, close to N200A. Color, inner perianth, median segment: When opening, upper surface: Towards the apex, close to N78A; towards the base, close to N78D; stripes, close to N200A. When opening, lower surface: Towards the apex, close to N78A and at the apex, close to 197A; towards the base, close to N78D; stripes, close to 200A. Fully opened, upper surface: Close to N80B; towards the apex, close to N81A; stripes, close to N200A; color does not change with development. Fully opened, lower surface: Close to N80D and N80B; at the apex, close to NN137C; stripes, close to N79A. Color, outer perianth, lateral segments: When opening, upper surface: Towards the apex, close to N81A; mid-section and base, close to N79A. When opening, lower surface: Close to N80A; at the apex, close to 137A; venation, close to 137A. Fully opened, upper surface: Close to N80A; mid-section and base, close to 79A; color does not change with development. Fully opened, lower surface: Close to N80A; at the apex, close to 137A; venation, close to 137A. Color, outer perianth, median segment: When opening, upper surface: Towards the apex, close to N81A; mid-section and base, close to N79A. When opening, lower surface: Close to N80A; at the apex, close to 137A; venation, close to 137A. Fully opened, upper surface: Close to N81B; mid-section and base, close to N79A; color does not change with development. Fully opened, lower surface: Close to N80A; at the apex, close to 137A; venation, close to 137A.

*Pedicels*.—Length: About 1.5 cm to 3.5 cm. Diameter: About 3 mm to 4 mm. Strength: Strong. Angle: Erect to about 80° from vertical. Texture: Smooth, glabrous. Color, upper and lower surfaces: Close to NN137A tinged with close to 187B.

*Reproductive organs*.—Stamens: Quantity per flower: Six. Anther shape: Oval. Anther size: About 2 mm by 7 mm. Anther color: Close to N199B. Pollen amount: Abundant. Pollen color: Close to 202A. Pistils: Quantity per flower: One. Pistil length: About 3.9 cm. Style length: About 3.5 cm. Style color: Close to 77A; towards the apex, close to N79C; towards the base, close to 69C. Stigma color: Close to N80A. Ovary color: Close to 146B.

*Fruits and seeds*.—Fruit and seed development has not been observed on plants of the new *Alstroemeria*.

Disease & pest resistance: Plants of the new *Alstroemeria* have not been observed to be resistant to pathogens and pests common to *Alstroemeria* plants.

Garden performance: Plants of the new *Alstroemeria* have been observed to have good garden performance and to tolerate wind, rain and temperatures ranging from about 6° C. to about 35° C.

It is claimed:

1. A new and distinct *Alstroemeria* plant named 'Koncareply' as illustrated and described.

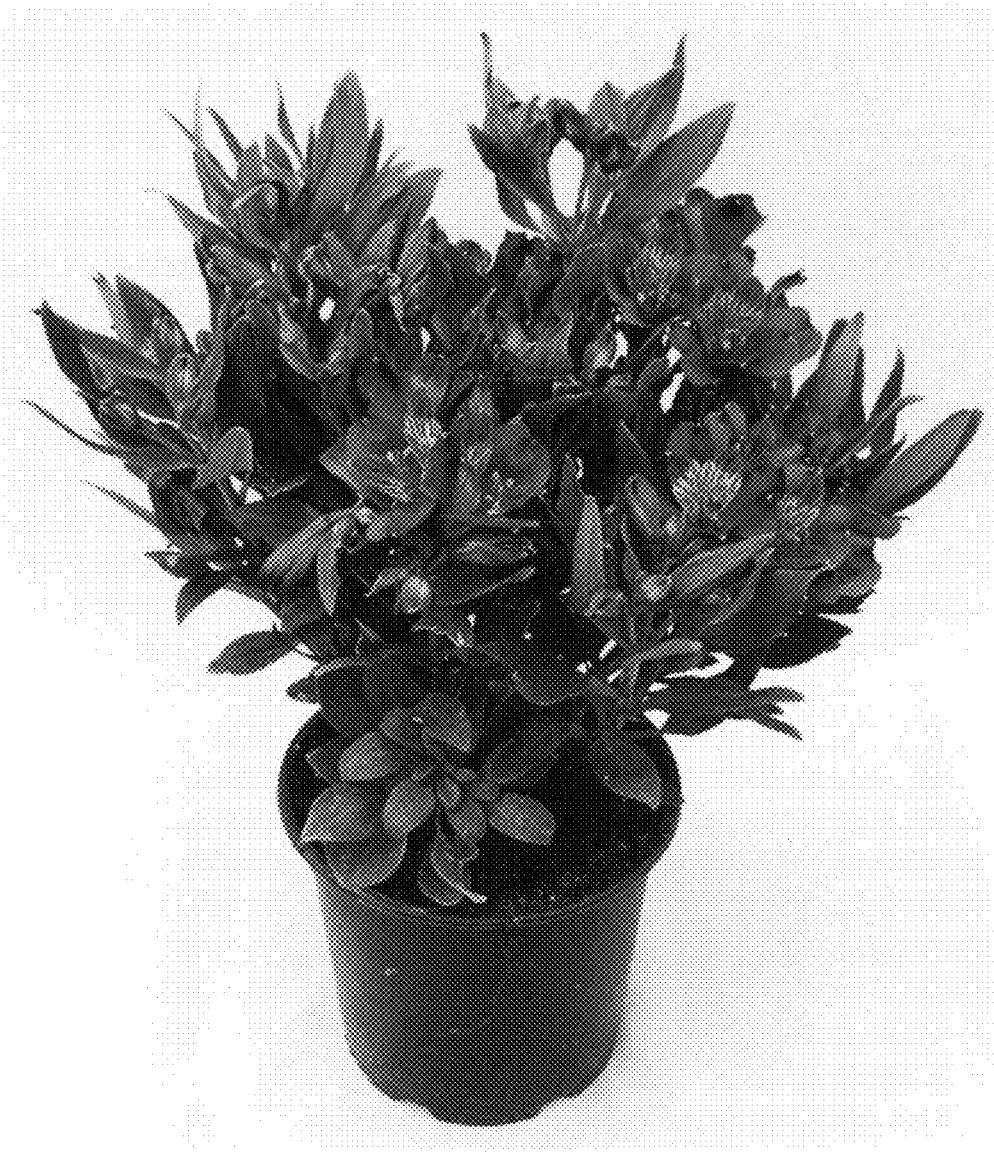

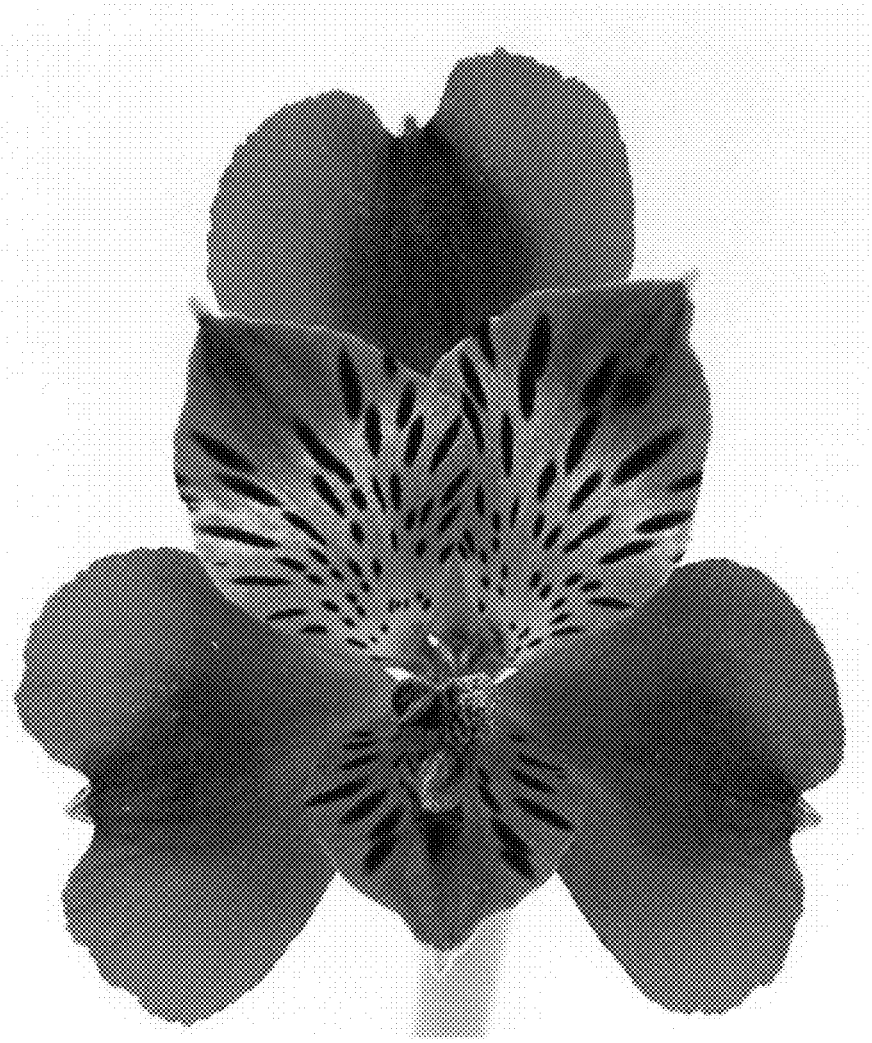

* * * * *